(12) United States Patent
Ogawa et al.

(10) Patent No.: US 9,913,971 B2
(45) Date of Patent: Mar. 13, 2018

(54) CONNECTOR

(71) Applicant: TERUMO KABUSHIKI KAISHA, Tokyo (JP)

(72) Inventors: Shinichi Ogawa, Fuefuki (JP); Yasuhiro Ueda, Kofu (JP); Kaori Funatsu, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 309 days.

(21) Appl. No.: 14/666,345

(22) PCT Filed: Sep. 28, 2012

(86) PCT No.: PCT/JP2012/075015
§ 371 (c)(1),
(2) Date: Mar. 24, 2015

(87) PCT Pub. No.: WO2014/049810
PCT Pub. Date: Apr. 3, 2014

(65) Prior Publication Data
US 2015/0297880 A1    Oct. 22, 2015

(51) Int. Cl.
*A61M 39/00* (2006.01)
*A61M 39/10* (2006.01)
(Continued)

(52) U.S. Cl.
CPC ........ *A61M 39/105* (2013.01); *A61M 39/045* (2013.01); *A61M 39/1011* (2013.01);
(Continued)

(58) Field of Classification Search
CPC ...... A61M 2039/262; A61M 2039/266; A61M 39/045; A61M 39/24; A61M 39/26; A61M 39/105; A61M 39/1011
(Continued)

(56) References Cited

U.S. PATENT DOCUMENTS

| 7,708,027 B2 | 5/2010 | Yokota et al. |
| 2006/0140798 A1 | 6/2006 | Kutsuzawa |

(Continued)

FOREIGN PATENT DOCUMENTS

| JP | 2002-306610 | 10/2002 |
| JP | 2003-144546 | 5/2003 |

(Continued)

OTHER PUBLICATIONS

The extended European Search Report dated May 9, 2016, by the European Patent Office in corresponding European Patent Application No. 12885852.9-1662. (7 pages).
(Continued)

*Primary Examiner* — Phillip Gray
(74) *Attorney, Agent, or Firm* — Buchanan Ingersoll & Rooney PC

(57) ABSTRACT

A connector includes: a port in which a disc configured to be displaceable is provided; a space defined by a side wall surrounding the disc in the circumferential direction when the disc is displaced and a bottom wall arranged at a position opposite the disc and configured to allow displacement of the disc; and a flow passage connected to the bottom wall at a position away from the side wall, and allowing fluid to flow therethrough to the space. The connector further includes cutouts formed from the flow passage to the side wall.

9 Claims, 8 Drawing Sheets

(51) Int. Cl.
*A61M 39/04* (2006.01)
*A61M 39/22* (2006.01)
*A61M 39/26* (2006.01)
*F16K 11/085* (2006.01)
*A61M 39/24* (2006.01)

(52) U.S. Cl.
CPC .......... *A61M 39/223* (2013.01); *A61M 39/24* (2013.01); *A61M 39/26* (2013.01); *F16K 11/0853* (2013.01); *A61M 2039/229* (2013.01); *A61M 2039/242* (2013.01); *A61M 2205/581* (2013.01); *A61M 2206/20* (2013.01)

(58) Field of Classification Search
USPC ........................................................ 604/533
See application file for complete search history.

(56) References Cited

U.S. PATENT DOCUMENTS

| | | |
|---|---|---|
| 2006/0184140 A1 | 8/2006 | Okiyama |
| 2007/0218745 A1 | 9/2007 | Yokota et al. |
| 2008/0172003 A1* | 7/2008 | Plishka ............... A61M 39/045 604/249 |
| 2010/0007134 A1 | 1/2010 | Elton et al. |

FOREIGN PATENT DOCUMENTS

| | | |
|---|---|---|
| JP | 2004-105574 | 4/2004 |
| JP | 2005-095577 | 4/2005 |
| JP | 3719443 B2 | 9/2005 |
| JP | 4744440 B2 | 8/2011 |
| WO | WO 02/064077 | 8/2002 |
| WO | WO 2004/101061 | 11/2004 |
| WO | 2008/043069 A2 | 4/2008 |
| WO | 2008/048777 A2 | 4/2008 |

OTHER PUBLICATIONS

International Search Report (PCT/ISA/210) dated Dec. 25, 2012, by the Japanese Patent Office as the International Searching Authority for International Application No. PCT/JP2012/075015.

\* cited by examiner

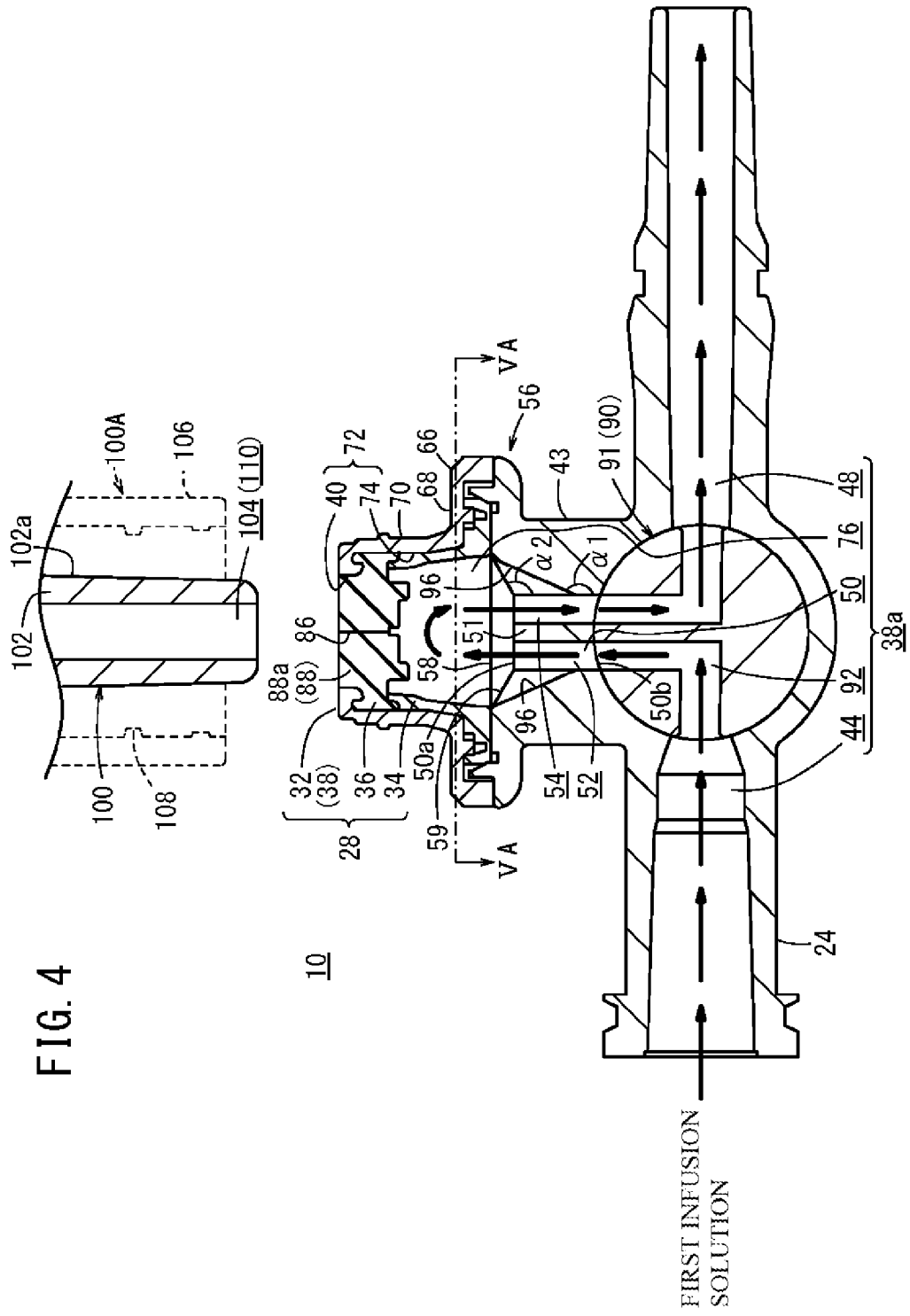

CONNECTOR

CROSS-REFERENCES TO RELATED APPLICATIONS

This application claims priority as a continuation application under 35 U.S.C. § 120 to International Application No. PCT/JP2012/075015 filed on Sep. 28, 2012, the entire content of which is incorporated herein by reference.

TECHNICAL FIELD

The present disclosure relates to a connector, for example, for interconnecting a plurality of tubes in a manner in which they cooperate to form an infusion line for infusion into a patient.

BACKGROUND DISCUSSION

Conventionally, in order to provide for infusion into a patient, a plurality of tubes are interconnected to structure an infusion line for fluid flow from an infusion bag to a patient. The plurality of tubes are interconnected through a connector. Upon infusion, a main infusion solution may be infused into a patient through a main line, and another line may be provided to supply another infusion solution therethrough. The other infusion solution may be mixed with the main infusion solution at the connector and guided to the patient. In this case, the connector includes three ports through which the infusion solutions flow, and can also include a three-way stopcock or the like that can arbitrarily switch the flowing state of infusion solutions, such as in the connector disclosed in JP 3719443 B1.

The connector disclosed in JP 3719443 B1 includes first and second ports constituting a main line passage and a third port constituting a second line passage in its body. A cock (a switching part) configured to switch communication between the first to third ports is also provided in the body. Since a male connector of a second line has to be inserted into and connected to the third port, the third port defines a space connected to the main line passage in between the passages of the first and second ports and formed to have a larger diameter than the main line passage and a relatively large volume.

In a state where the male connector of the second line is not connected (i.e., the third port is closed), a phenomenon can occur in which fluid of the infusion solution or an air pocket stagnates in the space. Fluid stagnating in such a space (hereinafter also referred to as stagnating fluid) may lead to various unfavorable effects.

For example, when an infusion line is filled with an infusion solution to evacuate air before infusing an infusion solution into a patient, air bubbles may stagnate in the space. The remaining air bubbles may be unfortunately delivered to the patient together with the infusion solution upon infusion of the infusion solution into the patient. In addition, when highly nutritious liquid is supplied as an infusion solution, stagnation of this liquid in the space may increase germs in the connector, and the germs may be unfortunately delivered to a patient. Further, upon switching of infusion solutions to be supplied to a patient, a previous infusion solution may be left in the space when a next infusion solution is supplied, and thus different infusion solutions may be undesirably mixed and delivered to a patient.

In order to reduce the possibility of these and other unfavorable effects resulting from stagnating fluid in the space, a connector can be structured to divert infusion solution flowing through the inner passage and guide the infusion solution to the space. The infusion solution guided to the space forces stagnating fluid to flow, and thus facilitates discharge of the stagnating fluid from the space.

Meanwhile, the connector disclosed in JP 3719443 B1 has a space larger than the inner passage, and thus a step part is formed on the boundary between the inner passage and the space. In such a connector, infusion solution doesn't flow toward the step part of the space even when the infusion solution is guided to the space, and so the connector can have a problem in that stagnating fluid still remains at the step part. In particular, a connector applied in an infusion line may be used in various orientations and the third port may point up or may be sideways, for example. Therefore, depending on the orientation of the connector in use, a relatively large amount of stagnating fluid may stagnate at the step part of the space, and the unfavorable outcomes caused by stagnating fluid as described above are not sufficiently reduced.

SUMMARY

The present disclosure is made in view of the above circumstances, and an object thereof is to provide a connector capable of greatly suppressing generation of stagnating fluid in the space with a simple structure even when the connector is used in various orientations, and thus enhancing safety of infusion and satisfactorily supply desired fluid.

In order to achieve the object as described above, a disclosed connector includes a port in which a disc configured to be displaceable is provided; a space provided in the port, and defined by a side wall surrounding the disc in a circumferential direction when the disc is displaced and a bottom wall arranged at a position opposite the disc and configured to allow displacement of the disc; a flow passage connected to the bottom wall at a position away from the side wall and configured to allow fluid to flow therethrough to the space; and cutouts formed from the flow passage to the side wall.

Since the connector described above includes cutouts formed from the flow passage to the side wall of the space, it is possible to guide fluid along the cutouts to the side wall, and reduce stagnating fluid that tends to be generated near the side wall. In addition, even when the connector is used with the port thereof positioned sideways, fluid can flow through the cutouts to the lower part and upper part of the space where stagnating fluid teds to be generated, thereby suppressing generation of stagnating fluid. Therefore, the connector can greatly suppress generation of stagnating fluid regardless of orientation of the port. Thus, safety of infusion can be enhanced and desired fluid can be satisfactorily supplied.

The cutouts are preferably groove parts respectively inclining by a larger angle than a connecting angle between the flow passage and the bottom wall.

Since the cutouts incline by a larger angle than a connecting angle between the flow passage and the bottom wall as described above, fluid can be guided smoothly from the flow passage to the side wall of the space.

In addition, it is preferable that the space be formed in a cylindrical shape by the side wall, an opening where the flow passage communicates with the bottom wall be formed as a long hole having a predetermined width, and each of the cutouts be formed to include a central part in a longitudinal direction of the opening and connected thereto.

Since each of the cutouts is formed to include the central part in the longitudinal direction of the opening of the flow passage and connected thereto as described above, when fluid flows into the space, the fluid can be guided to the side wall of the space at a position farthest from the opening of the flow passage. Therefore, generation of stagnating fluid can be further suppressed.

Further, it is preferable that the flow passage include an inflow passage allowing the fluid to flow therethrough to the space, and an outflow passage positioned across a partition from the inflow passage and configured to allow the fluid to flow from the space, and the cutouts be formed at symmetrical positions respectively in the inflow passage and the outflow passage across the partition.

Since the cutouts are formed at symmetrical positions respectively in the inflow passage and the outflow passage across the wall part as described above, fluid which has flowed from one of the cutouts connected to the inflow passage flows along the side wall of the space and then smoothly flows out from the outflow passage to which the other cutout is connected. Therefore, stagnation of fluid in the space can be suppressed and generation of stagnating fluid can be further reduced.

BRIEF DESCRIPTION OF DRAWINGS

FIG. 4 is a side sectional view illustrating a state where a male connector is not connected to the connector illustrated in FIG. 2.

DETAILED DESCRIPTION

Hereinafter, embodiments a connector according to the present disclosure will be described in detail based on the relation with an infusion set to which the connector can be applied. Application of the connector, of course, are not limited to infusion sets.

Figure 1:
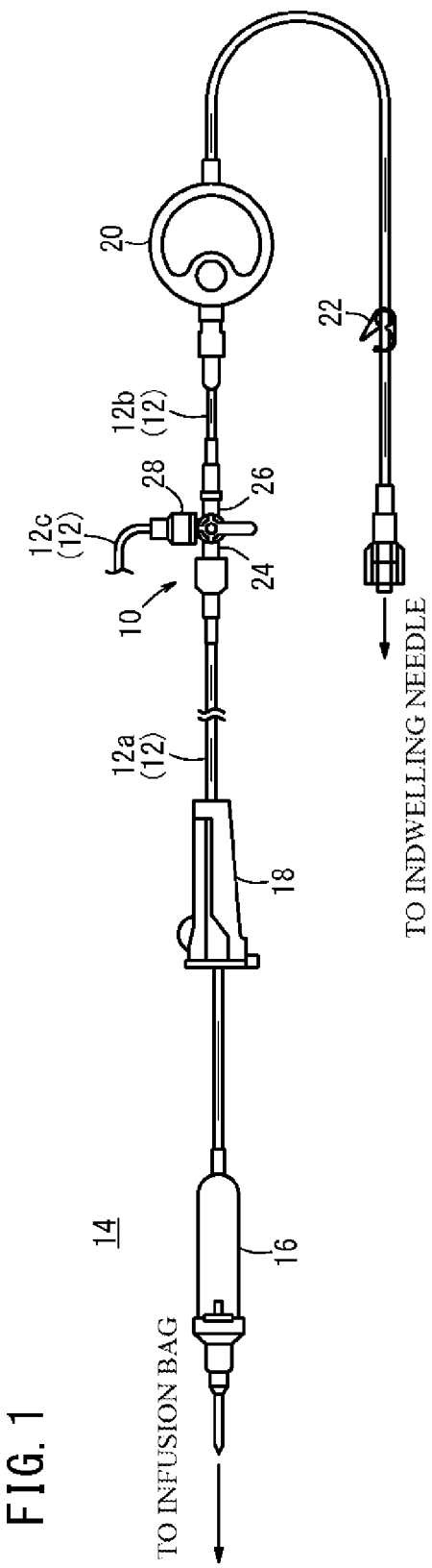
FIG. 1 is an explanatory drawing schematically illustrating an example of an infusion set to which a connector according to an embodiment is applied.

A connector 10 has a function to connect a plurality of tubes 12 in an infusion line for infusing into a patient as described above, and is applied, for example, to an infusion set 14 illustrated in FIG. 1. The upstream side of the infusion set 14 is connected to an infusion bag, which is not illustrated, and the downstream side thereof is connected to an indwelling needle, which is not illustrated. Thus, the infusion set 14 is constructed as an infusion line for administering infusion solution from an infusion bag to a patient.

Infusion solution flowing through the infusion set 14 can be any fluid, which may be administered to living bodies, such as liquid medicine, electrolyte solution for correction, physiological salt water. When the infusion solution is liquid medicine, various medicaments such as sedative, intravenous anesthetic, anesthetic type analgesic, local anesthetic, nondepolarizing muscle relaxant, vasopressor, depressor, coronary vasodilator, diuretic, antiarrhythmic agent, bronchodilator, hemostatic, vitamin preparation, antibiotic, and fat emulsion may be selected.

The tube 12 of the infusion set 14 is provided with, for example, a drip tube 16 configured to allow view of the flow rate of an infusion solution supplied from an infusion bag, a pinchcock 18 configured to regulate flow rate of infusion solution, an air vent filter 20 configured to discharge air in the infusion line (or supply air into the infusion line), and a clamp 22 configured to close the tube 12. The infusion set 14, of course, is not limited to the construction illustrated in FIG. 1. Various members provided on an infusion line (for example, an infusion pump and a check valve) may be included in the infusion set 14 in addition to the above-described members.

The tube 12 of the infusion set 14 is a flexible pipe body and constituting a passage of infusion solution. When the connector 10 is applied to the infusion set 14 described above, the connector 10 is positioned, for example, between the pinchcock 18 and the air vent filter 20. Specifically, the connector 10 connects a first tube 12a extending downstream from the drip tube 16 and a second tube 12b extending upstream from the air vent filter 20 so as to allow flow therebetween, thereby constituting a passage of the main line. To the connector 10, a third tube 12c constituting a second line is also connected, whereby the connector 10 allows communication between the main line and the second line inside the connector 10.

The position of the connector 10 is not limited as described above and can be provided at a desired position in the infusion set 14. The number of the connector 10 provided in the infusion set 14 (infusion line) is not limited to one but may be more than one.

Figure 2:
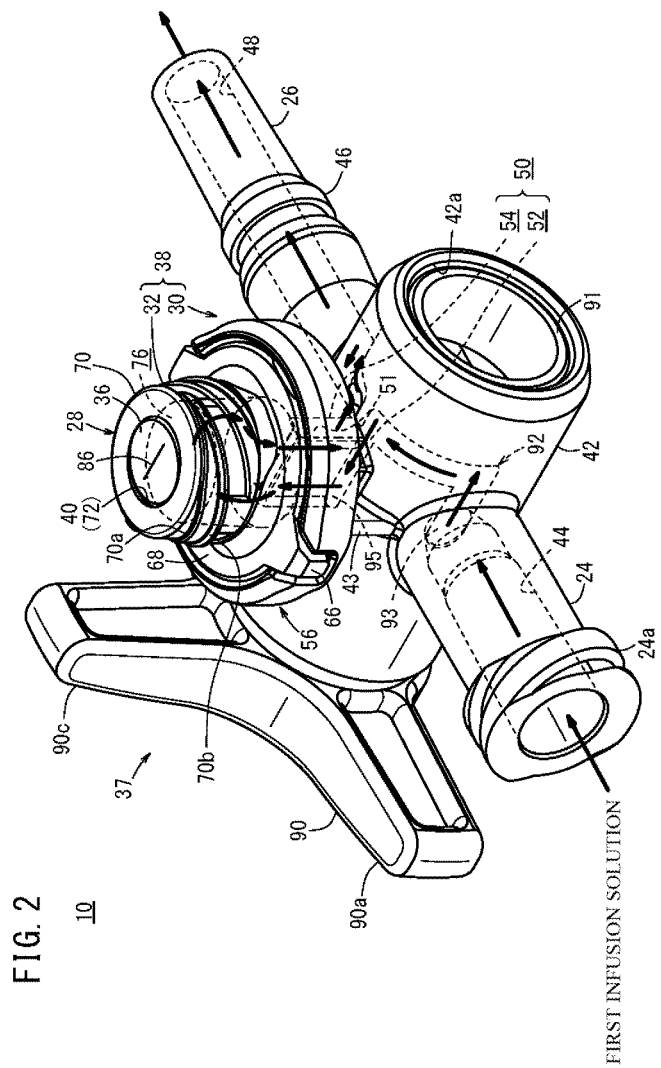
FIG. 2 is a perspective view illustrating whole structure of the connector illustrated in FIG. 1.

The specific configuration of the connector 10 according to the present embodiment will be described in detail. The connector 10 includes a first port 24, a second port 26, and a third port 28. To the first port 24, the first tube 12a constituting the main line is connected. To the second port 26, the second tube 12b also constituting the main line is connected. To the third port 28, the third tube 12c constituting the second line is connected. As illustrated in FIG. 2, the first and second ports 24 and 26 are provided in a housing 30 (enclosure) constituting a main part of the connector 10. The third port 28 is constituted of a cap 32 (lid), a support 34 (refer to FIG. 3), and a disc 36, which are members other than the housing 30. The third port 28 is constructed by assembling the other members to the housing 30.

Into the housing 30, a cock 37 is inserted rotatably. The cock 37 is rotated with respect to the housing 30 by a user and has a function to switch the communication state between the first to third ports 24, 26, and 28. Specifically, the connector 10 is constituted as a three-way stopcock capable of switching flow state of infusion solution flowing through the first to third tubes 12a to 12c under rotating operation of the cock 37.

The housing 30 and the cap 32 are connected to each other, constituting a body 38 of the connector 10. The body 38 has a passage 38a (refer to FIG. 4) of infusion solution inside the body 38. The support 34 and the disc 36 are housed in the body 38, and only the upper surface of the disc 36 is exposed from an opening 40 of the cap 32.

The housing 30, the cap 32, the support 34, and the cock 37 of the connector 10 are molded of a resin material in view of easiness of molding process and cost reduction. As the resin material, a material having higher rigidity than the tube 12 is preferably used. For example, polyethylene, polypropylene, polyolefin such as ethylene-vinyl acetate copolymer, polyurethane, polyamide, polyester, polycarbonate, polybutadiene, or polyvinyl chloride may be used.

Figure 3:
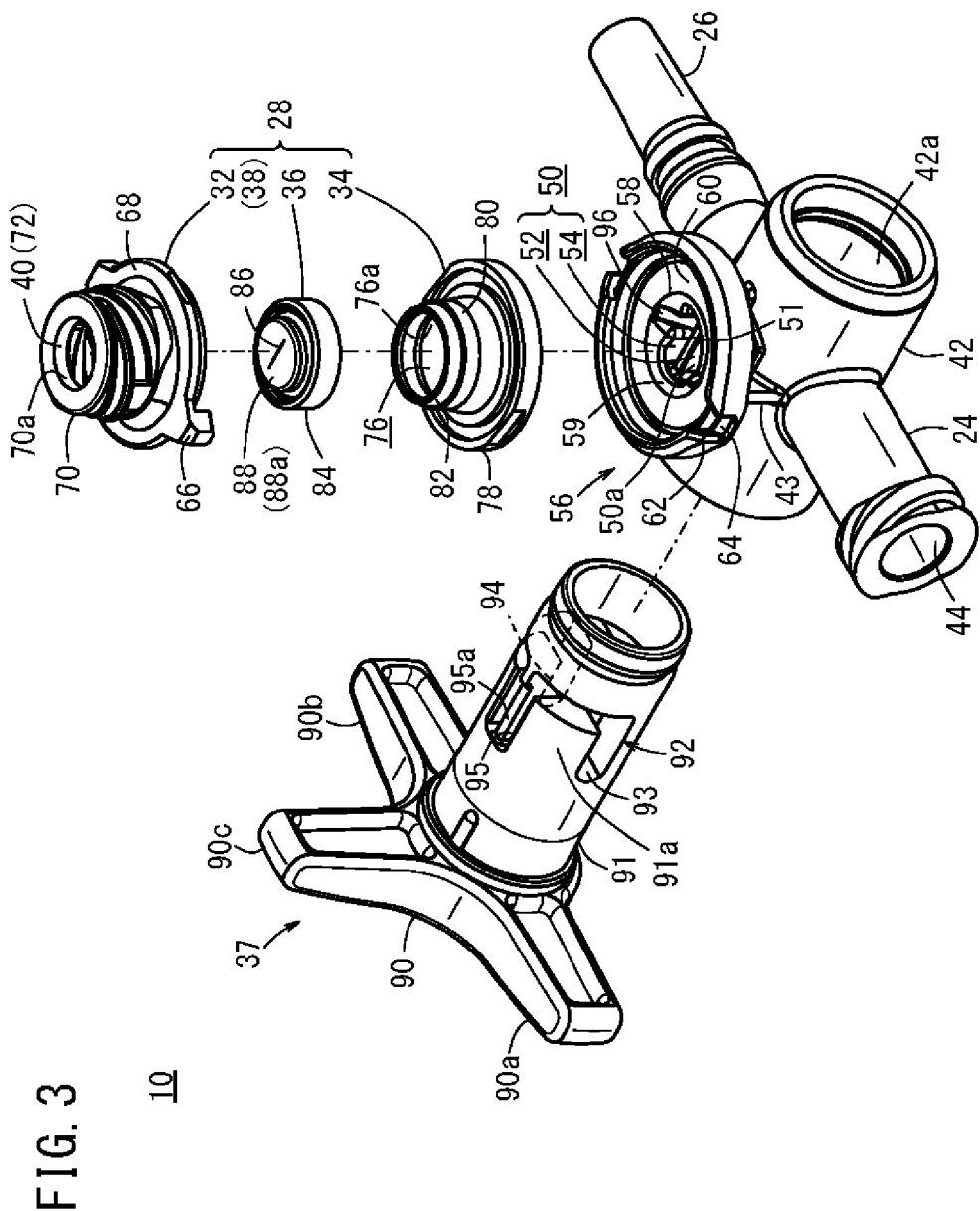
FIG. 3 is an exploded perspective view illustrating whole structure of the connector illustrated in FIG. 2.

As illustrated in FIGS. 2 and 3, the housing 30 includes a cylindrical part 42 at the center. The cylindrical part 42 is a connection base of the first to third ports 24, 26, and 28. The housing is structured such that the cock 37 is inserted into the cylindrical part 42. The first and second ports 24 and 26 are connected to the side peripheral surface of the cylindrical part 42. The first port 24 is formed in a cylindrical shape, and extends straight from the cylindrical part 42 to the upstream of the main line. Inside the first port 24, a first port passage 44, through which infusion solution can flow, extends along the axis direction. At the extension end of the first port 24, a connection end 24a is formed. The connection end 24a projects outward in a radial direction of the first port 24 and can be screwed with a male connector (not illustrated) of the first tube 12a.

Meanwhile, the second port 26 extends straight toward the downstream of the main line from a position opposite to the first port 24 across the cylindrical part 42. Inside the second port 26, a second port passage 48, through which infusion solution can flow, extends along the axis direction. Specifically, the first and second ports 24 and 26 are formed to have axes that are coincident with each other and align.

The second port 26 is thinner than the first port 24, formed as a male luer taper having a gradually reducing diameter toward the extension end, and inserted into the second tube 12b (bore). On the outer peripheral surface of the second port 26, a projection 46 is formed near the cylindrical part 42 along the circumferential direction. The second tube 12b and the second port 26 can be connected liquid-tightly by entering the second tube 12b beyond the projection 46.

The cylindrical part 42 of the housing 30 is formed to have a thickness allowing connection support of the first and second ports 24 and 26 and a shaft 91 of the cock 37 to be housed inside the cylindrical part 42. In addition, on the outer peripheral surface of the cylindrical part 42, a third port support 43 is formed at a position 90° apart from the first and second ports 24 and 26 in the circumferential direction. The third port support 43 extends outward in a radial direction by a predetermined length. The body of the cylindrical part 42 extends in a direction, which is orthogonal to a plane including the axes of the first and second ports 24 and 26 and the axis of the third port support 43. Inside the cylindrical part 42, an insertion hole 42a is formed through the cylindrical part 42 along the extension direction, and the cock 37 is inserted from one end of the cylindrical part 42 in the extension direction.

The cock 37 includes a handle 90, which can be operated by a user, and the shaft 91 connected to the handle 90. The handle 90 includes first, second, and third extension parts 90a, 90b, and 90c extending from the central part connected to the shaft 91 to form a "T" shape. The first to third extension parts 90a to 90c are respectively structured to indicate flow state of, the first to third ports 24, 26, and 28. For example, when the first to third extension parts 90a to 90c coincide with the extension directions of the first to third ports 24, 26, and 28 (the state illustrated in FIG. 2), the first to third ports 24, 26, and 28 communicate with one another inside the housing 30, and a first infusion solution flowing through the main line and a second infusion solution flowing through the second line can converge (hereinafter, the state of FIG. 2 may be referred to as a state where all ports are in communication). For example, when the cock 37 is rotated by 90°, the first extension part 90a coincides with the extension direction of the third port 28 and the third extension part 90c coincides with the extension direction of the second port 26. In this state, only the third port 28 and the second port 26 communicate with each other inside the housing 30 and the first infusion solution supplied from the first port 24 is shut off, thus the second infusion solution supplied from the third port 28 is discharged through to the second port 26.

The shaft 91 of the cock 37 is in contact with the insertion hole 42a of the cylindrical part 42 slidably, rotatably, and liquid-tightly. A guide groove 92 having a predetermined shape is formed in the outer peripheral surface of the shaft 91. In the cylindrical part 42 with the shaft 91 inserted therein, the first and second infusion solutions are guided based on the shape (channel) of the guide groove 92.

The guide groove 92 has a first end 93, a second end 94, and a third end 95 in the generally central part in the axis direction of the shaft 91 at positions corresponding respectively to the first to third extension parts 90a to 90c. The guide groove 92 extends from one end toward the extension end of the shaft 91, which is opposite to the handle 90, by a predetermined length, bends at the position, and extends from the bending part in the circumferential direction to be connected to a bending part of another end. Thus, the guide groove 92 is formed in a crank shape. The first end 93 and the third end 95 are disposed at positions away from each other by 90° in the circumferential direction, and the second end 94 and the third end 95 are disposed at positions away from each other by 90°. Between the respective ends lie peripheral walls 91a of the shaft 91. In particular, as illustrated in FIG. 3, a peripheral wall lies between the first end 93 and the third end 95, and another peripheral wall lies between the second end 94 and the third end 95.

In the state where the cock 37 is inserted in the cylindrical part 42 as illustrated in FIG. 2, passages in the housing 30 (the first port passage 44, the second port passage 48, and an inner passage 50 of the third port support 43) face the shaft 91. Accordingly, when the first to third extension parts 90a to 90c coincide with the extension direction of the first to third ports 24, 26, and 28 (in the state where all ports are in communication), respective ends of the guide groove 92 face the passages in the housing 30, allowing communication between the passages in the housing 30 through the respective ends of the guide groove 92. On the other hand, rotation of the cock 37 from the state where all ports are in communication with respect to the cylindrical part 42 by 45° makes the passages in the housing 30 face the peripheral walls 91a of the shaft 91, whereby the passages in the housing 30 are shut off by the shaft 91. Meanwhile, the housing 30 and the cock 37 may be provided with a structure configured to provide a user with click feeling when the user rotates the cock 37 by a predetermined angle (e.g. 45°).

The third port 28 of the connector 10 is supported by the third port support 43 at a position away from the cylindrical part 42 with a predetermined spacing. Inside the third port support 43, the inner passage 50 (i.e., flow passage) configured to allow communication between the cylindrical part 42 and the third port 28 is formed as illustrated in FIGS. 3 and 4. Specifically, a lower opening 50b of the inner passage 50 communicates with the insertion hole 42a of the cylindrical part 42, and the inner passage 50 is switched to communicate with/be shut off from the guide groove 92 based on the orientation of the cock 37 inserted in the insertion hole 42a. An upper opening 50a of the inner passage 50 communicates with a space (a through hole 76) formed in the third port 28.

At the upper part of the third port support 43, a mounting part 56 for mounting the cap 32 and the support 34 thereon is provided. The mounting part 56 is formed in a shape of disk pedestal expanding outward in the diameter direction. The mounting part 56 includes a circular exposure opening 58 through which the upper opening 50a of the inner passage 50 is exposed in the central part of the upper surface, an arrangement part 60 formed in a flat shape surrounding the exposure opening 58, and locked walls 62 and groove parts 64 formed on the first and second ports 24 and 26 outside the arrangement part 60. The mounting part 56 is structured such that the support 34 is placed on the arrangement part 60, and locking claws 66 of the cap 32 are locked at the locked walls 62.

The exposure opening 58 is formed to have a diameter larger than the width of the upper opening 50a of the inner passage 50. Between the upper opening 50a of the inner passage 50 and the edge of the exposure opening 58, a stopper part 59 inclined at a predetermined angle is formed. The stopper part 59 has a function to prevent the male connector 100 of the third tube 12c from passing through a slit 86 of the disc 36 by limiting the elastic deformation of the disc 36 below a predetermined level when the male connector 100 is inserted into the third port 28 (also refer to FIG. 5B).

The third port 28 is a connection terminal constituted of the cap 32, the support 34, and the disc 36 as described above. When the third port 28 is fixedly connected to the mounting part 56, the third port 28 is provided in a direction perpendicular to the axis direction of the first and second ports 24 and 26. To the third port 28, the male connector 100 (insert) of the third tube 12c is connected.

As illustrated in FIGS. 2 and 4, the cap 32 is formed to have an outer shape capable of housing the disc 36 inside thereof, and being connected to the male connector 100 of the third tube 12c. The cap 32 includes a flange part 68 on the lower side, which is connected to the mounting part 56, and a terminal part 70 extending in the upper direction by a predetermined length from the flange part 68.

The flange part 68 is formed to have an outer diameter covering the arrangement part 60 of the mounting part 56. At predetermined symmetrical positions on the peripheral edge of the flange part 68 across the terminal part 70, the pair of locking claws 66 projecting outward in a radial direction are connected thereto. The pair of locking claws 66 is formed in a hook shape to have spacing slightly shorter than that of the pair of locked walls 62. Thus, the locking claws are structured to be locked at the locked walls 62 by fitting the pair of locking claws 66 in the groove parts 64 of the cylindrical part 42.

The terminal part 70 is formed in a cylindrical shape having a diameter smaller than the flange part 68. Inside the terminal part 70, a hole part 72 is formed along the axis direction (vertical direction). At the upper side of the hole part 72, the opening 40 having a narrower diameter toward the inner side is formed. At the lower side of the opening 40, there is provided a housing part 74, which is formed to have a diameter larger than the opening 40 and is capable of housing the support 34 and the disc 36.

The opening 40 is structured to have a predetermined internal diameter (an internal diameter allowing the disc 36 to be inserted when the opening 40 is surrounded by a ring-shaped projection 70a projecting downward from the upper edge of the terminal part 70. In addition, on the outer peripheral surface of the terminal part 70, a helical projecting line 70b for screwing the luer lock type male connector is formed.

The male connector 100 of the third tube 12c to be connected to the connector 10 as the second line of the infusion set 14 is now described with reference to FIG. 4. As the male connector 100, for example, a luer slip type male connector according to a selected ISO standard can be used. Specifically, the male connector 100 includes an insertion cylinder 102 inserted in the connector 10 (the cap 32).

The insertion cylinder 102 extends linearly in the axis direction and is structured such that the distal end (lower end in FIG. 4) of the insertion cylinder 102 pushes open the slit 86 of the disc 36 when the insertion cylinder 102 comes in contact with the connector 10. Inside the insertion cylinder 102, a flow passage 104 is formed. Through the flow passage 104, the second infusion solution supplied from the third tube 12c flows. Specifically, the flow passage 104 is structured as a passage for the second line (hereinafter, referred to as the second line passage 110).

The outer peripheral surface of the insertion cylinder 102 is formed to have a tapered surface 102a reduced in diameter toward the distal end. Specifically, when the insertion cylinder 102 is inserted into the connector 10 by a predetermined length, the body part of the insertion cylinder 102 at the opening 40 of the cap 32 has an outer diameter matching the internal diameter of the opening 40. The insertion cylinder 102 is formed to have a slightly smaller outer diameter than the body part at the distal end. When the insertion cylinder 102 proceeds into the connector 10, the tapered surface 102a fits with the opening 40, whereby connection to the third port 28 (the cap 32, the support 34, and the disc 36) is made.

A male connector to be connected to the third port 28, of course, is not limited to the male connector 100 of the luer slip type as described above. For example, as illustrated by a broken line in FIG. 4, a luer lock type male connector 100A provided with a connection cylinder 106 surrounding the insertion cylinder 102 and having a helical projection 108, which is provided on the inner peripheral surface of the connection cylinder 106 and screwed onto the helical projecting line 70b of the cap 32.

Meanwhile, the support 34 of the third port 28 has a function to support the disc 36 at a predetermined distance from the inner passage 50. Specifically, upon connection between the third port 28 and the male connector 100, a space for inserting the male connector 100 (the insertion cylinder 102) by a length more than a certain length is needed. The support 34 supports the disc 36 at the upper part thereof, and constructs the space by the through hole 76 extending vertically.

The support 34 includes a flange 78 placed on the arrangement part 60 of the mounting part 56, and a supporting cylinder 80 projecting upward from the upper surface of the flange 78. The outer diameter of the upper part of the supporting cylinder 80 is structured as a holding part 82 having a diameter smaller than the body part. On the outside of the holding part 82, a fixing part 84 of the disc 36 can be fitted. The fixing part 84 can take the form, for example, of an annular cylindrical wall, as illustrated in FIG. 3.

The through hole 76 is formed to run through the inside of the flange 78 and the supporting cylinder 80. The through hole 76 communicates with the exposure opening 58 in a state where the support 34 is placed on the arrangement part 60. Specifically, the through hole 76 is formed as a space enclosed by a side wall 76a surrounded in the circumferential direction by the support 34, the stopper part 59 (bottom wall) formed to surround the exposure opening 58, and the disc 36 arranged to oppose the stopper part 59.

The through hole 76 is structured as a passage inside the third port 28, and to/from the through hole 76, the first infusion solution flows from/into the inner passage 50. Specifically, the passage 38a in the body 38 is constituted of the first and second port passages 44 and 48, the guide groove 92, the inner passage 50, and the through hole 76. In addition, the through hole 76 is formed to allow movement of the insertion cylinder 102 and the elastic deformed disc 36 as the insertion cylinder 102 is inserted. Thus, the through hole 76 and the opening 40 are structured as a space to allow displacement of the disc 36.

The disc 36 of the third port 28 is molded with elastic material unlike other members, providing elastic force capable of elastic deformation as the male connector 100 is inserted. An elastic material used to form the disc 36 can be synthetic rubber such as polybutadiene, nitrile, or chloroprene, natural rubber such as polyisoprene, thermoset elastomer such as urethane rubber, silicone rubber, or fluorine rubber, thermoplastic elastomer, or other elastomer, for example, but the elastic material is not particularly limited thereto.

The disc 36 has the slit 86, which is opened/closed as the male connector 100 is inserted/extracted, in the central part and has a function to allow communication with the second line passage 110 and shut off the second line passage 110 by opening and closing the slit 86. The disc 36 is formed in a disc shape having a relatively large thickness, and includes the fixing part 84 held between the cap 32 and the support 34 and an inner deformation part 88 connected to the fixing part 84. In the upper part of the deformation part 88, an upper bulged part 88a inserted into the opening 40 is formed.

The slit 86 is formed to penetrate through the deformation part 88 in the vertical direction, and is closed in a state where the upper bulged part 88a is housed in the opening 40 (a state where the deformation part 88 is not elastically deformed). The slit 86 is gradually opened as the deformation part 88 is displaced (elastically deformed) relative to the fixing part 84 as the male connector 100 is pushed into the slit 86.

In the third port 28, the through hole 76 below the deformation part 88 is hollow in a state where the male connector 100 is not inserted, and air before priming, the first infusion solution flowing through the inner passage 50, and the like tends to stagnate in the through hole 76. Therefore, the connector 10 is structured to discharge stagnating fluid by guiding the first infusion solution from the cylindrical part 42 through the inner passage 50 to the through hole 76. Hereinafter, the structure to discharge stagnating fluid will be described in detail.

Figure 5A:
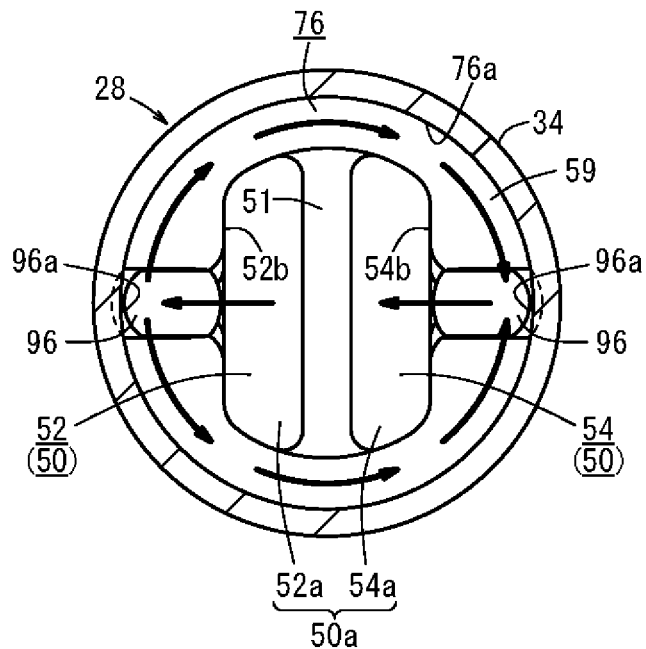
FIG. 5A is a partial sectional view of the connector illustrated in FIG. 4 taken along line VA-VA.

As illustrated in FIGS. 2 and 5A, the inner passage 50 is formed to have a slightly longer side in the extending direction of the cylindrical part 42 in planar view, and in the central part in the short direction, a partition 51 that divides the inner passage 50 into two passages (an inflow passage 52 and an outflow passage 54) is formed. At the third end 95 of the guide groove 92 of the cock 37, a guide wall 95a dividing the guide groove 92 is formed along the axis direction of the shaft 91 (refer to FIG. 3) corresponding to the partition 51. The guide wall 95a has a function to guide the first infusion solution flowing from the first end 93 through the guide groove 92 to the inflow passage 52 of the third port support 43. Thus, the first infusion solution flows through the inflow passage 52 into the through hole 76, and then is discharged from the through hole 76 to the outflow passage 54 across the partition 51.

The inflow passage 52 and the outflow passage 54 are formed to be long holes that are symmetrical about the partition 51 in planar view (refer to FIG. 5A). An upper opening 52a of the inflow passage 52 and an upper opening 54a of the outflow passage 54 are connected to a lower side of the inclined stopper part 59.

In order to facilitate understanding of passages in the connector 10, flow of infusion solutions in a state where all ports are in communication will be described with reference to FIGS. 2, 4, and 5B. The first infusion solution flows from the first tube 12a into the first port passage 44, and flows through the first port passage 44 to the cylindrical part 42 side. In the cylindrical part 42, the first infusion solution flows from the first end 93 into the guide groove 92, and flows along the crank shape of the guide groove 92 to the third end 95 (the guide groove 92 illustrated in FIG. 4 is schematic illustration). At the third end 95, the first infusion solution is guided upward (to the third port 28 side) by the guide wall 95a, thereby flowing through the inflow passage 52 of the third port support 43 to the through hole 76.

When the male connector 100 is not connected to the third port 28, the first infusion solution flows inside the through hole 76 and then flows into the outflow passage 54. The first infusion solution then flows through the outflow passage 54 into the third end 95, and flows along the crank shape of the guide groove 92 to the second end 94. The first infusion solution flows from the second end 94 into the second port passage 48, and finally discharged from the second port passage 48 to the second tube 12b.

Figure 5B:
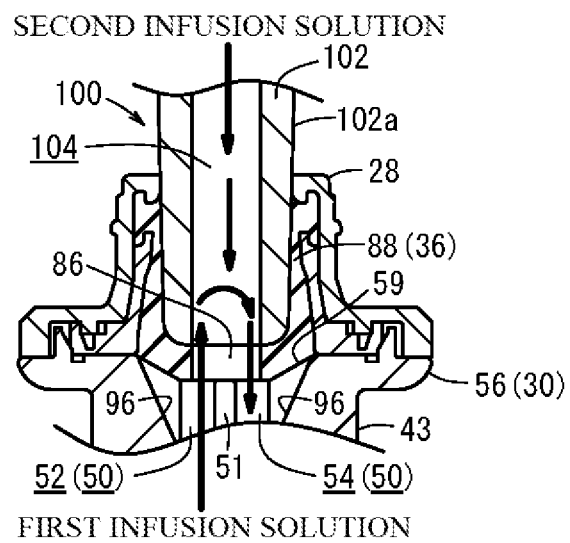
FIG. 5B is a partial side sectional view illustrating a state where the male connector is connected to a third port of the connector illustrated in FIG. 2.

On the other hand, when the male connector 100 is connected to third port 28, the slit 86 is opened by the insertion cylinder 102 inserted in the through hole 76 as illustrated in FIG. 5B. The insertion of the insertion cylinder 102 stops when the disc 36 is pushed into the vicinity of the upper opening 50a of the inner passage 50 because the stopper part 59 limits elastic deformation of the disc 36. Thus, the slit 86 is positioned in the vicinity of the upper opening 50a of the inner passage 50, causing the first infusion solution moving through the inflow passage 52 to smoothly flow from the inflow passage 52 into the flow passage 104, whereby the first infusion solution is mixed with the second infusion solution supplied through the flow passage 104. The mixed first and second infusion solutions are smoothly discharged from the flow passage 104 to the outflow passage 54.

Meanwhile, the upper opening 50a of the inner passage 50 is formed narrower compared to the lower section of the through hole 76, and between the side wall 76a constituting the through hole 76 and the opening 52a of the inner passage 50, the stopper part 59 structured as the bottom wall of the through hole 76 is interposed. When the opening 52a is connected to the bottom wall at a position away from the side wall 76a as described above, stagnating fluid tends to stagnate on the side wall 76a side of the through hole 76 (also refer to FIGS. 6C and 6D). However, the connector 10 according to the present embodiment includes cutout grooves 96 (cutout), thereby realizing smooth discharge of stagnating fluid.

As illustrated in FIGS. 4 and 5A, the cutout grooves 96 are formed respectively for the inflow passage 52 and the outflow passage 54. Specifically, the cutout grooves 96 in a pair are connected to the inner passage 50. The pair of cutout grooves 96 and 96 is formed in wall parts 52b and 54b respectively constituting the inflow passage 52 and the outflow passage 54 and opposing the partition 51, and formed in the central part in the longitudinal direction of the inflow passage 52 and the outflow passage 54.

In the cutout grooves 96, the deep sides opposing the partition 51 in planar view have an arc shape and extend from positions in the vicinity of the insertion hole 42a of the inflow passage 52 and the outflow passage 54 to the stopper part 59 with some inclination. In other words, the cutout grooves 96 are formed in taper shapes gradually deepened toward the through hole 76. At the boundary portion of the through hole 76, deepest parts 96a (the tops of the arc shapes of the cutout grooves 96) are connected to the side wall 76a.

Thus, the cutout grooves 96 can guide infusion solution flowing through the inflow passage 52 and the outflow passage 54 to the side wall 76a of the through hole 76. Because the sectional areas of the cutout grooves 96 are sufficiently narrower than the sectional areas of the inflow passage 52 and the outflow passage 54, the cutout grooves 96 can guide infusion solution to the side wall 76a and also speed up the infusion solution which has flowed into the cutout grooves 96. Therefore, when the first infusion solution flowing through the cutout groove 96 of the inflow passage 52 flows from the cutout groove 96 into the through hole 76, the first infusion solution flows through the through hole 76 along the side wall 76a side. As a result, the first infusion solution turns on the side wall 76a of the through hole 76 in the circumferential direction (refer to FIG. 5A) and also proceeds on the side wall 76a along the axis direction (refer to FIG. 4), and then turns along the bottom surface of the disc 36 to the opposite side wall 76a. Thus, fluid can easily flows in the vicinity of the inner surface where stagnating fluid tends to stagnate in the through hole 76.

The inclination angle α1 of the cutout grooves 96 connected to the wall parts 52b and 54b of the inflow passage 52 and the outflow passage 54 is larger than the inclination angle α2 of the stopper part 59 connected to the wall parts 52b and 54b. Therefore, the first infusion solution which has flowed into the inflow passage 52 can enter the cutout groove 96 at an early stage and can flow smoothly to the side wall 76a of the through hole 76.

The connector 10 according to the present embodiment is basically structured as described above, and operation and effect thereof will be described. Note that a case where only the first and second tubes 12a and 12b are connected will be described in detail because the connector 10 can provide larger effect when the third tube 12c is not connected.

Figure 6A:
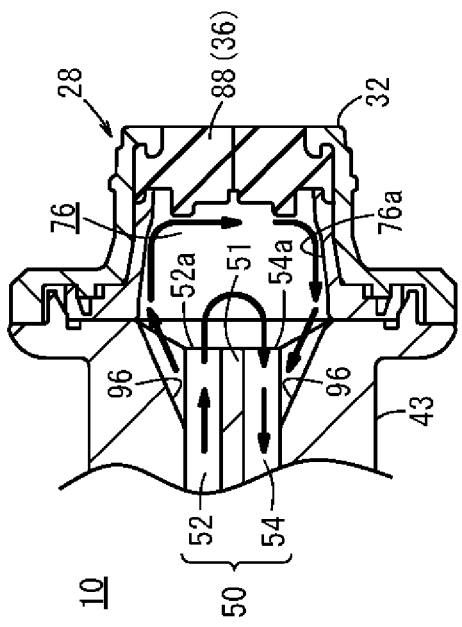
FIG. 6A is a partial side sectional view illustrating flow of a first infusion solution in a state where the third port illustrated in FIG. 4 points up.
Figure 6B:
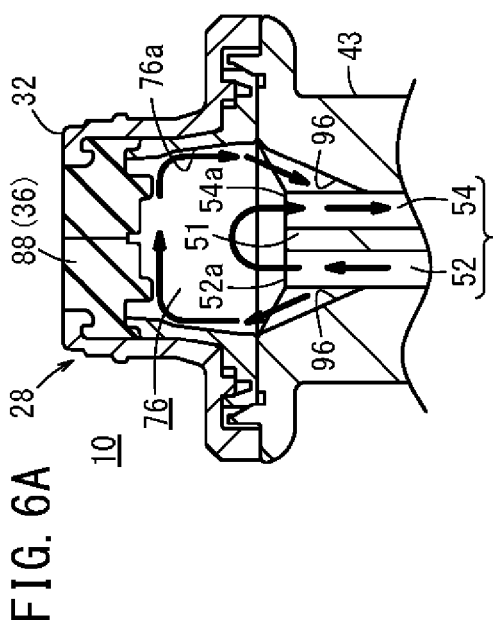
FIG. 6B is a partial side sectional view illustrating flow of the first infusion solution in a state where the third port illustrated in FIG. 4 is sideways.
Figure 6C:
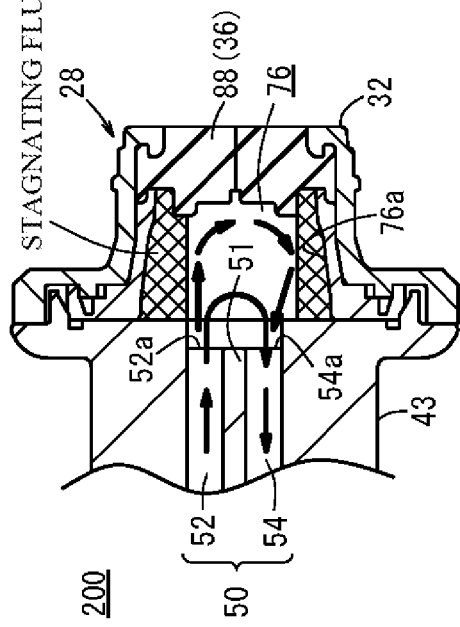
FIG. 6C is a partial side sectional view illustrating flow of the first infusion solution in a state where a third port of a conventional connector points up.
Figure 6D:
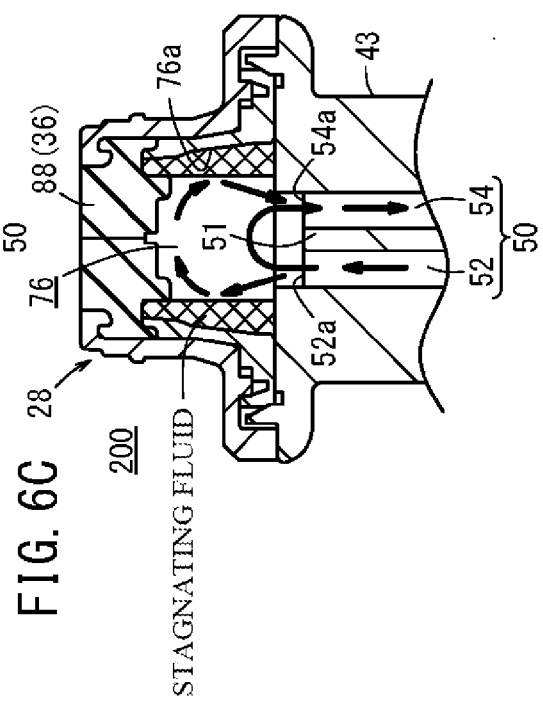
FIG. 6D is a partial side sectional view illustrating flow of the first infusion solution in a state where the third port of the conventional connector is sideways.

First, based on FIGS. 6C and 6D, a conventional connector 200, in which no cutout groove 96 is formed, specifically, in which a step part is formed between the inner passage 50 and the side wall 76a will be briefly described. In the description below, components that are similar to or that have similar functions to those of the connector according to the present embodiment are denoted by the same references and redundant detailed description thereof will be avoided.

When the third port 28 of the connector 200 points up as illustrated in FIG. 6C, the first infusion solution which has flowed from the inflow passage 52 into the through hole 76 flows along the inflow direction to the disc 36 side and turns to the outflow passage 54 side through the lower side of the disc 36. Therefore, flowing force of the first infusion solution is hardly transmitted to the vicinity of the side wall 76a of the through hole 76, tending to generate stagnating fluid near the side wall 76a. In FIGS. 6C and 6D, portions where stagnating fluid tends to be generated will be indicated by mesh hatching.

When the third port 28 of the connector 200 is sideways as illustrated in FIG. 6D, stagnating fluid tends to stagnate more around the lower part of the side wall 76a of the through hole 76 due to gravity since a step part is formed between the inner passage 50 and the side wall 76a, which is unfavorable. In addition, since the first infusion solution positively acts to flow in the gravity direction, fluid lighter than the first infusion solution such as air tends to stagnate more near the upper part of the side wall 76a of the through hole 76.

On the other hand, the connector 10 according to the present embodiment has the cutout grooves 96 from the inflow passage 52 and the outflow passage 54 to the through hole 76. Therefore, when the third port 28 of the connector 10 points up as illustrated in FIG. 6A, the first infusion solution flowing through the cutout groove 96 flows towards the side wall 76a of the through hole 76. Therefore, the first infusion solution which has flowed from the cutout groove 96 to the through hole 76 turns along the side wall 76a and the bottom surface of the disc 36, whereby stagnating fluid that tends to be generated near the side wall 76a can be greatly suppressed.

The first infusion solution having turned in the through hole 76 easily enters into the outflow passage 54, to which the cutout groove 96 is connected. Specifically, the cutout groove 96 on the outflow passage 54 side is also formed to be connected to the side wall 76a, and thus, the first infusion solution having turned to the side wall 76a flows out from the cutout groove 96 of the outflow passage 54. Therefore, stagnation of the first infusion solution in the through hole 76 is suppressed and stagnating fluid generation can be further reduced.

In addition, when the third port 28 of the connector 10 is sideways as illustrated in FIG. 6B, the first infusion solution flowing through the cutout groove 96 is guided to turn in the vicinity of the side wall 76a of the through hole 76. Therefore, even when the third port 28 of the connector 10 is positioned sideways, stagnating fluid can be sufficiently suppressed.

As described above, according to the connector 10 of the present embodiment including the cutout groove 96 from the inner passage 50 and connected to the side wall 76a of the through hole 76, infusion solution can be guided along the cutout groove 96 to the vicinity of the side wall 76a of the through hole 76 due to the cutout grooves 96, whereby stagnating fluid tending to be generated near the side wall 76a can be reduced. In addition, even when the connector 10 is used with the third port 28 of the connector 10 positioned sideways, fluid can flow through the cutout grooves 96 to the lower part and upper part of the through hole 76 where stagnating fluid tends to be generated because the fluid, thereby suppressing generation of stagnating fluid. Therefore, the connector 10 can greatly suppress generation of stagnating fluid regardless of orientation of the third port 28 in use. Thus, safety of infusion can be enhanced and desired fluid can be satisfactorily supplied.

In addition, the cutout grooves 96 are formed to include the central part in the longitudinal direction of the opening 52a of the inflow passage 52 and the opening 54a of the outflow passage 54 and to be connected to the openings 52a and 54a. Thus, when, for example, the first infusion solution flows into the through hole 76, the first infusion solution can be guided to the side wall 76*a* of the through hole 76 at a position farthest from the opening 52*a*. Therefore, generation of stagnating fluid can be further suppressed.

Note that the cutouts of the connector 10 according to the present embodiment are not limited to have the structure described above and various structures can be, of course, applied. For example, the cutouts may be formed in a shape other than a groove shape and may be formed as holes communicating the inner passage 50 and the through hole 76.

Figure 7:
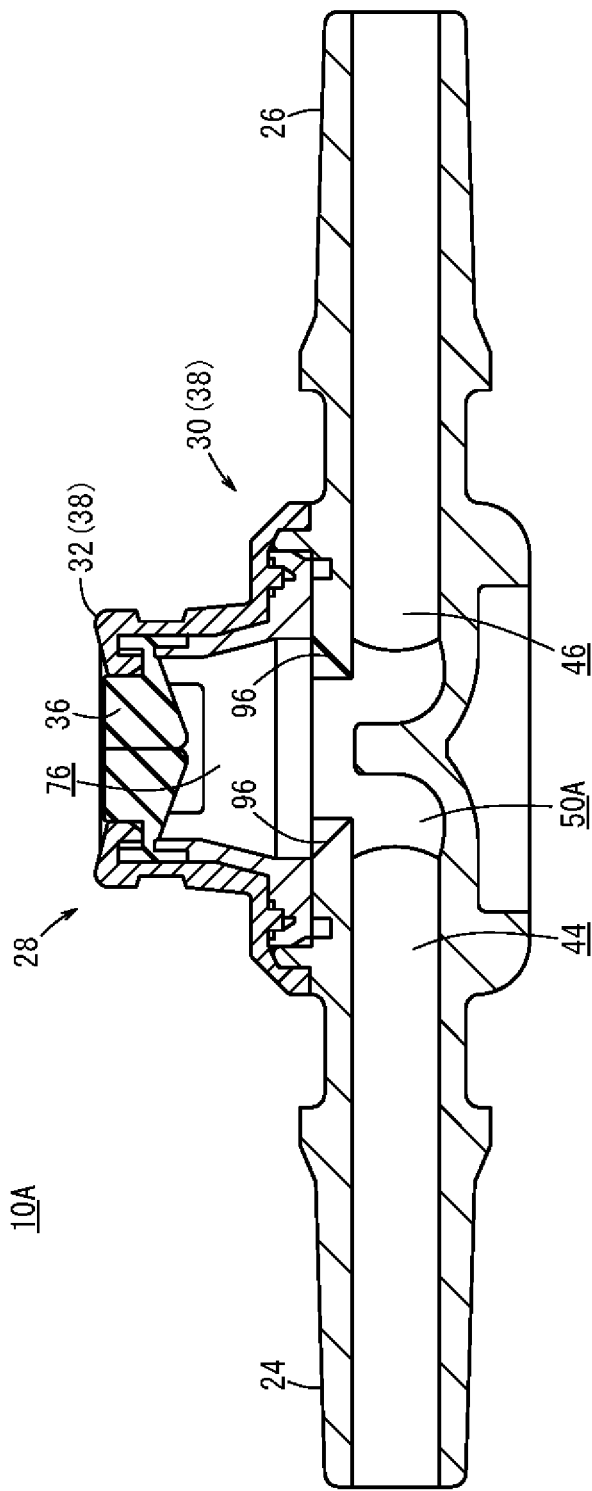
FIG. 7 is a side sectional view illustrating a connector according to a first variation.

In addition, a connector in which the cutout grooves 96 are formed is not limited to a three-way stopcock, of course. For example, as a connector 10A according to a first variation illustrated in FIG. 7, the cutout grooves 96 may be formed in a three-port connector (T port connector), in which the first port 24 and the second port 26 communicate through the inner passage 50A and the third port 28 is connected to the upper side of the inner passage 50A in communication therewith.

Figure 8A:
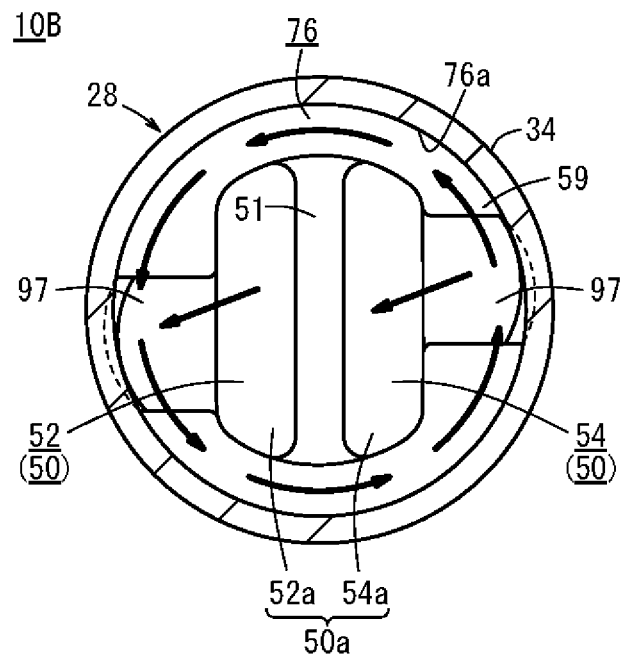
FIG. 8A is a partial plane sectional view illustrating the inside of a third port of a connector according to a second variation.

In a connector 10B according to a second variation illustrated in FIG. 8A, a cutout groove 97 connected to the inflow passage 52 is formed in an area from the central part to one end in the longitudinal direction of the inflow passage 52. The cutout groove 97 is formed so that the first infusion solution moves along the extending direction of the inflow passage 52 and closer to one end from the central part in the longitudinal direction, and structured such that the first infusion solution which has flowed to the through hole 76 turns along the circumferential direction of the side wall 76*a* of the through hole 76. Thus, the first infusion solution which has flowed to the through hole 76 can generate more dynamic flow (fluid turbulence), and thus can suppress generation of stagnating fluid. In this case, a cutout groove 97 connected to the outflow passage 54 is also formed in an area from the central part to the other end in the longitudinal direction of the outflow passage 54, whereby the first infusion solution can be satisfactorily discharged through the cutout groove 97.

Figure 8B:
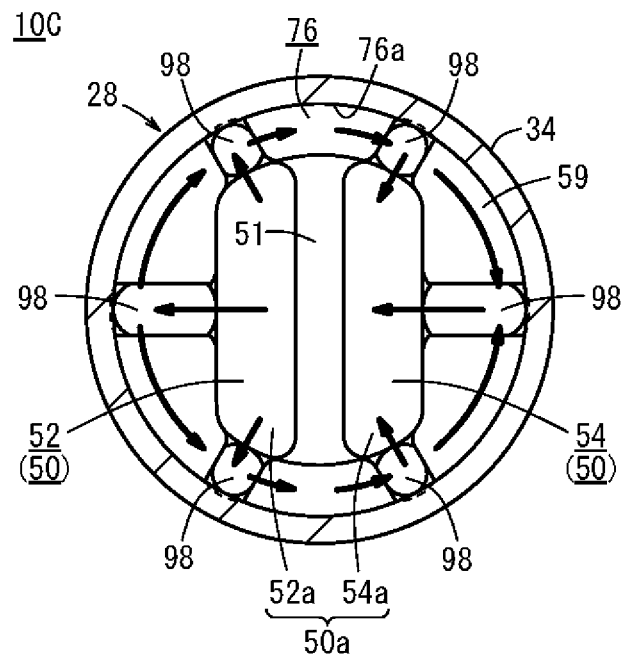
FIG. 8B is a partial plane sectional view illustrating the inside of a third port of a connector according to a third variation.

Further, a connector 10C according to a third variation illustrated in FIG. 8B has a structure, in which a plurality of (three in FIG. 8B) cutout grooves 98 is connected to each of the inflow passage 52 and the outflow passage 54. Even when the plurality of cutout grooves 98 is formed in each of the inflow passage 52 and the outflow passage 54, the first infusion solution can flow in the vicinity of the side wall 76*a* of the through hole 76, and thus generation of stagnating fluid can be suppressed.

The detailed description above describes a connector. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A connector comprising:
   a first port;
   a second port;
   a third port in which a disc is provided, said disc configured to be displaceable;
   a space provided in the third port, and defined by a side wall surrounding the disc in a circumferential direction when the disc is displaced and a bottom wall arranged at a position opposite the disc and configured to allow displacement of the disc;
   a flow passage connected to the bottom wall at a position away from the side wall and including an inflow passage allowing the fluid to flow therethrough from the first port to the space, and an outflow passage positioned across a partition from the inflow passage and configured to allow the fluid to flow therethrough from the space to the second port; and
   cutouts formed from the flow passage to the side wall.

2. The connector according to claim 1, wherein the cutouts are groove parts respectively inclining by a larger angle than a connecting angle between the flow passage and the bottom wall.

3. The connector according to claim 2, wherein the space is formed in a cylindrical shape by the side wall, an opening where the flow passage communicates with the bottom wall is formed as a long hole having a predetermined width, and each of the cutouts is formed to include a central part in a longitudinal direction of the opening and connected thereto.

4. The connector according to claim 1, wherein the cutouts are formed at symmetrical positions respectively in the inflow passage and the outflow passage across the partition.

5. The connector according to claim 2, wherein the cutouts are formed at symmetrical positions respectively in the inflow passage and the outflow passage across the partition.

6. The connector according to claim 3, wherein the cutouts are formed at symmetrical positions respectively in the inflow passage and the outflow passage across the partition.

7. A connector comprising:
   an interior space;
   a first port;
   a second port;
   a third port having a valve which is normally closed and is openable by pressure from outside the third port to thereby be displaced towards the interior space, wherein the interior space is defined by a bottom wall arranged at a position opposite the valve with respect to the interior space and an enclosed side wall disposed between the valve and the bottom wall;
   a flow passage connected to the bottom wall at a position away from the side wall and including an inflow passage allowing the fluid to flow therethrough from the first port to the interior space, and an outflow passage positioned across a partition from the inflow passage and configured to allow the fluid to flow therethrough from the interior space to the second port; and
   at least one groove formed in the flow passage and the side wall so as to extend from the flow passage to the side wall.

8. The connector according to claim 7, wherein the grooves define a larger angle with respect to a central axis of the flow passage than a connection angle between the flow passage and the bottom wall.

9. The connector according to claim 7, wherein the at least one groove comprises a plurality of grooves formed at symmetrical positions respectively in the inflow passage and the outflow passage across the partition.

* * * * *